(12) United States Patent
Peyman

(10) Patent No.: US 7,458,953 B2
(45) Date of Patent: Dec. 2, 2008

(54) OCULAR DRAINAGE DEVICE

(75) Inventor: Gholam A. Peyman, 10650 W. Tropicana Cir., Sun City, AZ (US) 85351

(73) Assignee: Gholam A. Peyman, Sun City, AZ (US)

( * ) Notice: Subject to any disclaimer, the term of this patent is extended or adjusted under 35 U.S.C. 154(b) by 168 days.

(21) Appl. No.: 11/425,275

(22) Filed: Jun. 20, 2006

(65) Prior Publication Data

US 2007/0293872 A1    Dec. 20, 2007

(51) Int. Cl.
*A61M 5/00* (2006.01)
*A61F 11/00* (2006.01)

(52) U.S. Cl. ............................. 604/9; 606/108; 606/153

(58) Field of Classification Search ............... 604/8, 604/9; 606/107, 108, 161; 623/4.1, 1.12; 424/422, 423

See application file for complete search history.

(56) References Cited

U.S. PATENT DOCUMENTS

| | | | |
|---|---|---|---|
| 4,079,038 A | 3/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |
| 4,304,767 A | 12/1981 | Heller et al. | |
| 4,457,757 A | 7/1984 | Molteno | |
| 4,750,901 A | 6/1988 | Molteno | |
| 4,946,931 A | 8/1990 | Heller et al. | |
| 5,071,408 A | 12/1991 | Ahmed | |
| 5,178,604 A | 1/1993 | Baerveldt et al. | |
| 5,300,020 A * | 4/1994 | L'Esperance, Jr. ............. | 604/9 |
| 5,362,478 A | 11/1994 | Desai et al. | |
| 5,397,300 A | 3/1995 | Baerveldt et al. | |
| 5,411,473 A | 5/1995 | Ahmed | |
| 5,439,686 A | 8/1995 | Desai et al. | |
| 5,476,445 A | 12/1995 | Baerveldt et al. | |
| 5,498,421 A | 3/1996 | Grinstaff et al. | |
| 5,558,629 A | 9/1996 | Baerveldt et al. | |
| 5,560,933 A | 10/1996 | Soon-Shiong et al. | |

(Continued)

FOREIGN PATENT DOCUMENTS

RU      2118142 C1 *   8/1998

OTHER PUBLICATIONS

Website http://www.ahmedvalve.com, New World Medical—The Ahmed Glaucoma Valve, 2004, 26 pgs.

(Continued)

*Primary Examiner*—Leslie R Deak
(74) *Attorney, Agent, or Firm*—Thompson Hine LLP

(57) ABSTRACT

An ocular fluid-draining device to remove fluid from the eye, for example, in a patient after glaucoma surgery. The device includes a shunt at least partially enclosed in a conduit, a portion of the conduit being collapsible or inwardly deformable to control, reduce, or prevent fluid flow. The distal end of the shunt and the conduit is positioned in the eye using a stylet. A reservoir is attached onto the proximal end of the shunt and the conduit. Applying pressure to the conduit cinches it to reduce or close the shunt; releasing this pressure opens the shunt to control the fluid flow from the anterior chamber to the reservoir. One or more components of the fluid draining device may contain medicaments and/or may be coated with amniotic membrane to provide additional desirable properties or effects.

20 Claims, 8 Drawing Sheets

U.S. PATENT DOCUMENTS

| | | | |
|---|---|---|---|
| 5,616,118 | A | 4/1997 | Ahmed |
| 5,665,382 | A | 9/1997 | Grinstaff et al. |
| 5,681,275 | A | 10/1997 | Ahmed |
| 5,785,674 | A | 7/1998 | Mateen |
| 5,811,510 | A | 9/1998 | Papisov |
| 5,863,990 | A | 1/1999 | Papisov |
| 5,916,596 | A | 6/1999 | Desai et al. |
| 5,968,543 | A | 10/1999 | Heller et al. |
| 6,096,331 | A | 8/2000 | Desai et al. |
| 6,261,256 | B1 | 7/2001 | Ahmed |
| 6,375,986 | B1 | 4/2002 | Ryde et al. |
| 6,413,536 | B1 | 7/2002 | Gibson et al. |
| 6,436,906 | B1 | 8/2002 | Or et al. |
| 6,440,942 | B1 | 8/2002 | Or et al. |
| 6,462,026 | B1 | 10/2002 | Or et al. |
| 6,506,405 | B1 | 1/2003 | Desai et al. |
| 6,528,067 | B1 | 3/2003 | Magdassi et al. |
| 6,537,579 | B1 | 3/2003 | Desai et al. |
| 6,592,903 | B2 | 7/2003 | Ryde et al. |
| 6,596,296 | B1 | 7/2003 | Nelson et al. |
| 6,613,355 | B2 | 9/2003 | Ng et al. |
| 6,667,371 | B2 | 12/2003 | Ng et al. |
| 6,699,210 | B2 * | 3/2004 | Williams et al. ............... 604/8 |
| 6,749,868 | B1 | 6/2004 | Desai et al. |
| 6,753,006 | B1 | 6/2004 | Desai et al. |
| 6,822,086 | B1 | 11/2004 | Papisov |
| 6,962,573 | B1 * | 11/2005 | Wilcox ..................... 604/9 |
| 7,008,396 | B1 * | 3/2006 | Straub ..................... 604/8 |
| 2002/0143284 | A1 * | 10/2002 | Tu et al. ..................... 604/9 |
| 2007/0249984 | A1 | 10/2007 | Molteno |

OTHER PUBLICATIONS

Website http://www.baerveldt.com, AMO—Baerveldt® Glaucoma Implant, 2004, 61 pgs.

Website http://www.molteno.com, Molteno Ophthalmic Ltd—Molteno Ophthalmic, prior to Jun. 23, 2006, 7 pages.

* cited by examiner

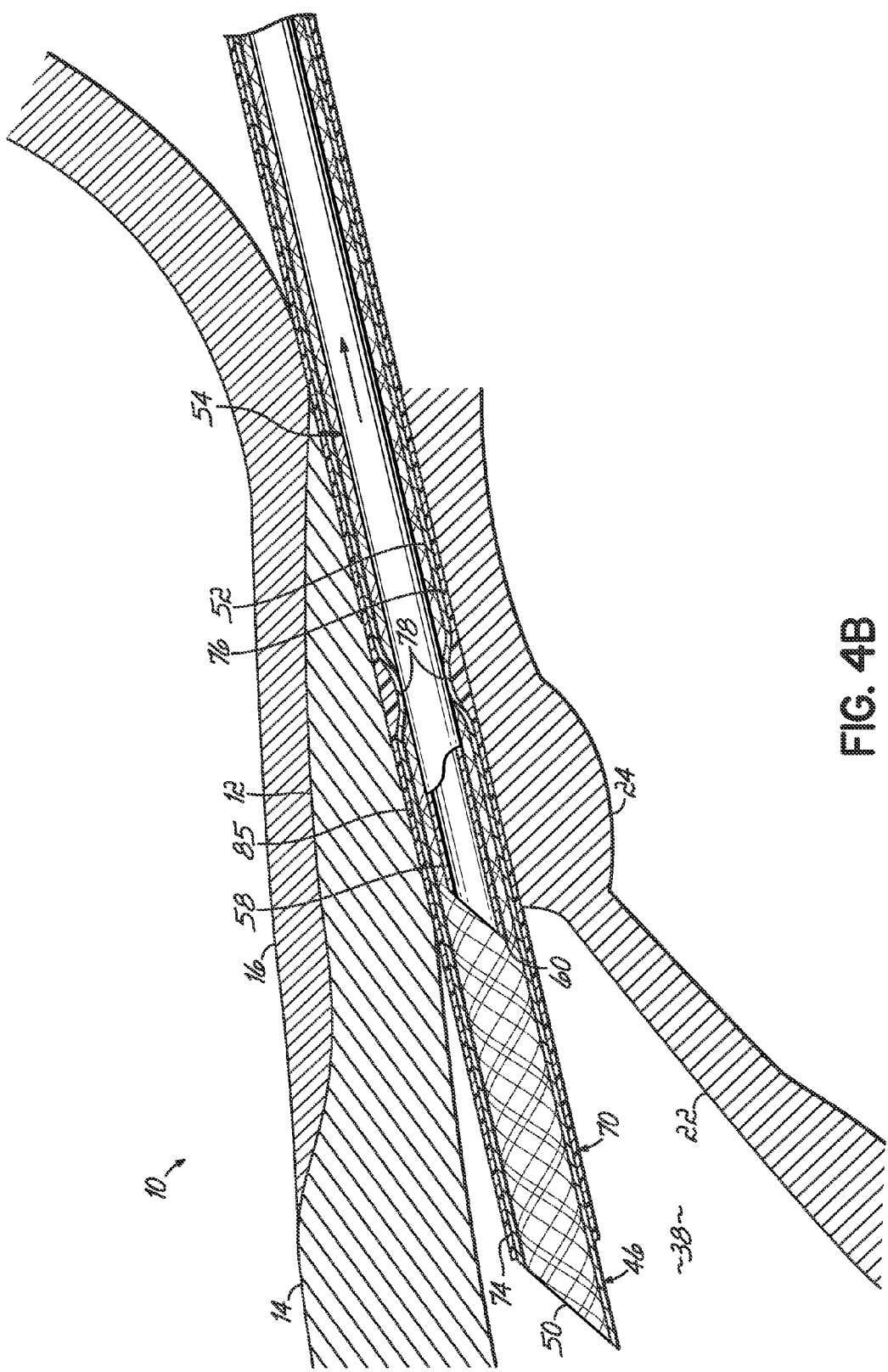

OCULAR DRAINAGE DEVICE

FIELD OF THE INVENTION

An ocular device and a method of using to drain fluid from an eye, e.g., following glaucoma surgery.

BACKGROUND

Glaucoma is a significant health problem effecting about three million people in the United States alone. It is a leading cause of blindness, with about ten percent of the treated cases still resulting in blindness. In addition, estimates assert that only about half of the cases are diagnosed, much less treated. While treatments are effective for lessening some of the symptoms of glaucoma, such as vision loss, there is currently no cure for glaucoma.

Because high intraocular pressure is the most common risk factor for glaucoma, many treatments attempt to lower the intraocular pressure using either drugs or surgery to open the trabecular network and drainage canals to drain fluid from the eye, or to slow fluid production in the eye.

Primary open-angle glaucoma (POAG) and angle closure glaucoma are the two most common types of glaucoma. Current surgical treatments for POAG include laser eye surgery and traditional eye surgery. One type of laser surgery is selective laser trabeculoplasty (SLT), using a laser beam to open select areas of the trabecular meshwork of the eye and thereby improve fluid flow out of the eye. Another type of laser surgery is argon laser trabeculoplasty (ALT), using a laser beam to open blocked or closed drainage canals and thereby improve fluid flow out of the eye. Drugs may be applied in combination with these therapies.

Current treatments for angle closure glaucoma include laser cyclophotocoagulation, which treats the ciliary body and thus reduces the production of fluid and decreasing the fluid volume to be removed.

Conventional surgery is generally used only after medication and laser surgery has failed or in an emergency situation. The most common procedure is filtering microsurgery, also known as trabeculectomy. One or more small incisions are made in the sclera, through which fluid flows out of the eye and is absorbed by the blood. A flap of tissue is left to cover the incisions.

While effective, patients may not tolerate surgery or may have factors for which surgery may not be effective (e.g., patients with neovascular glaucoma, glaucoma associated with uveitis, prior history of a failure with a filtering procedure, or a glaucoma patient under the age of 30). Such patients may require a tube shunt device to be implanted through which fluid drains from the eye. Examples of such devices include Ahmed™ glaucoma valves (New World Medical, Inc., CA) Baerveldt® glaucoma implants (Advanced Medical Optics, Inc., Santa Ana Calif.), or Molteno® glaucoma implants (Molteno Ophthalmic Ltd., Dunedin, New Zealand).

Shunt implant surgery requires multiple steps and difficulties exist with current devices. Moreover, it would be desirable to control of dispersion of the fluid that is removed from the eye, that is, to regulate its outflow. Failure to adequately regulate fluid release can lower intraocular pressure too rapidly, leading to a "soft" eye. In addition, cytokines in the aqueous humor can leak and accelerate the inflammatory process possibly, leading to scarring. Therefore, other devices and methods of using the devices are desirable.

BRIEF DESCRIPTION OF THE DRAWINGS

FIG. 4B illustrates the shunt of FIG. 2A implanted in the human eye with the stylet of FIG. 2B being removed.

DETAILED DESCRIPTION

A device and method of using the device for draining fluid from an eye after glaucoma surgery. Fluid includes aqueous fluid. Fluid may include vitreous fluid if a prior vitrectomy is performed.

In one embodiment, the device includes a shunt defining a lumen providing fluid communication between an interior chamber of the eye and an exterior of the eye. The device also includes a collapsible conduit operatively coupled to the shunt. A stylet is received into the lumen of the shunt for implanting the shunt and collapsible conduit into the eye. Fluid begins to drain upon the removal of the stylet. A reservoir is operatively coupled to the collapsible conduit. Fluid is drained from the interior chamber of the eye through the shunt and into the reservoir.

In another embodiment, the device includes a radially expandable shunt defining a lumen providing fluid communication between an interior chamber of the eye and an exterior of the eye. In addition, the device includes a collapsible conduit operatively coupled to the shunt. A reservoir is operatively coupled to the collapsible conduit for containing fluid transferred from the interior chamber of the eye through the shunt and into the reservoir.

In another embodiment, the device includes at least one of the reservoir, shunt, or collapsible conduit containing a medicament that can be eluted from the device, either in a controlled manner or at a constant rate.

In another embodiment, a method for implanting a device to drain fluid from the eye includes forming a small incision in the conjunctiva exposing the sclera. The sclera is cut to form a lamella extending from the anterior chamber backwards towards the retina. A shunt and collapsible conduit are combined and a stylet inserted inside the combination. The combination is implanted under the conjunctiva and/or scleral lamella into an interior chamber of the eye using the stylet to guide its placement. The conduit is then pressurized at one or more sites, the stylet removed, and a reservoir connected to the conduit. The reservoir is slid under the conjunctiva and the incision formed in the conjunctiva is closed.

Figure 1:
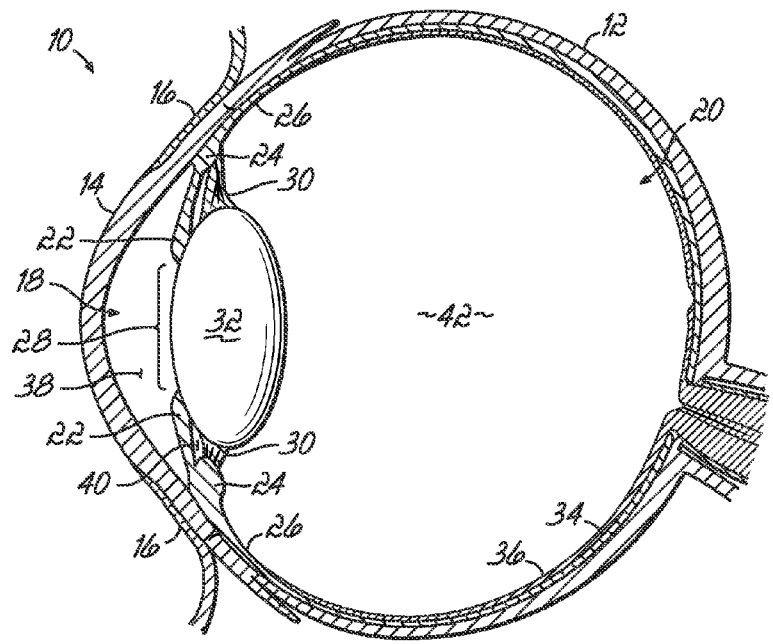
FIG. 1 illustrates a cross sectional view of the human eye.

Referring to FIG. 1, a cross section of the eye 10 is illustrated. The eye 10 is divided into three layers: the first external layer including the sclera 12, cornea 14, and conjunctiva 16; the second intermediate layer which is divided into the anterior section 18 and the posterior section 20; the anterior section 18 includes the iris 22 and the ciliary body 24, and the posterior section 20 includes the choroid 34; the third internal layer includes the retina 36. The anterior chamber 38 is defined between the cornea 14 and the iris 22 and contains aqueous fluid; the posterior chamber 42 id defined between the lens 32 and the retina 36 contains vitreous fluid.

Aqueous fluid is produced by the epithilium lining in the ciliary body 24 and flows through the pupil 28 into the anterior chamber 38. The trabecular meshwork then drains the aqueous fluid to Schelmm's canal where it is deposited into the venous system. All eyes have some intraocular pressure caused by the flow resistance of the aqueous humor passing through Schelmm's canal. However, when there is excess fluid volume to be removed or when removal is obstructed, the accumulated aqueous fluid may result increased intraocular pressure, resulting in glaucoma.

Figure 2A:
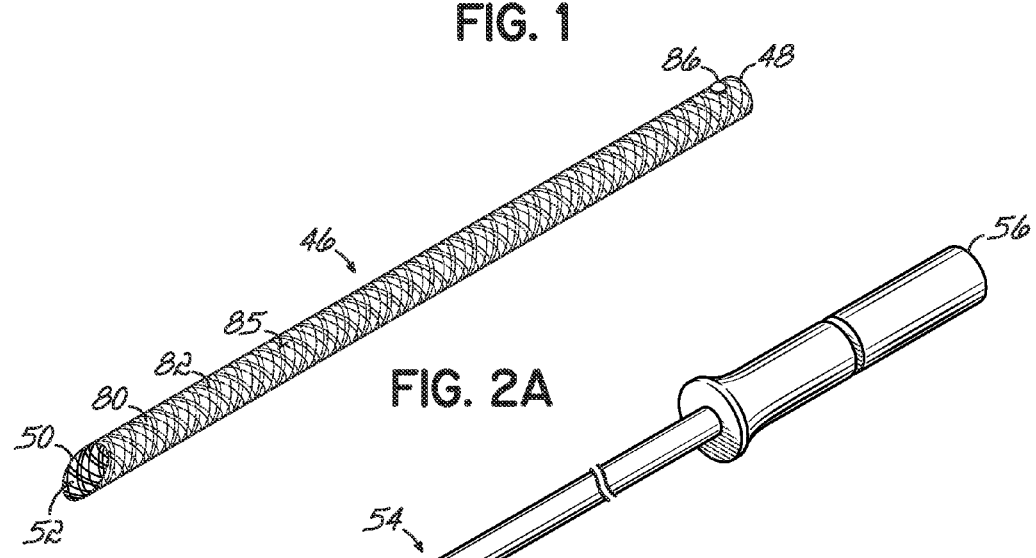
FIG. 2A illustrates one embodiment of an expandable shunt.
Figure 2B:
FIG. 2B illustrates one embodiment of a stylet.
Figure 2C:
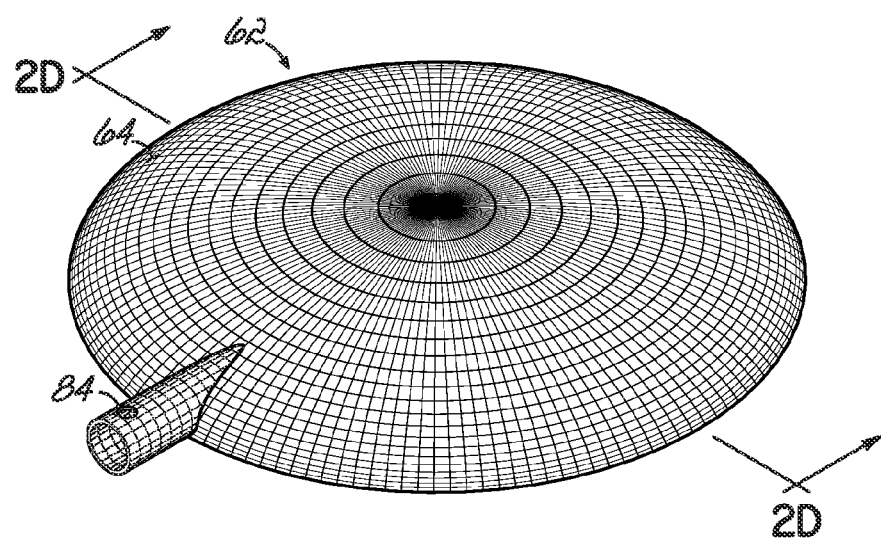
FIG. 2C illustrates one embodiment of a reservoir.
Figure 2D:
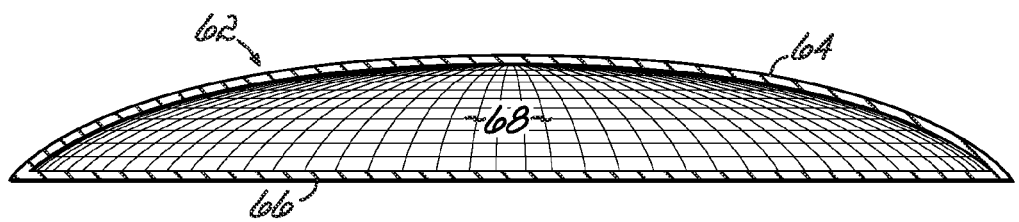
FIG. 2D illustrates a cross-sectional view of the reservoir of FIG. 2C.
Figure 2E:
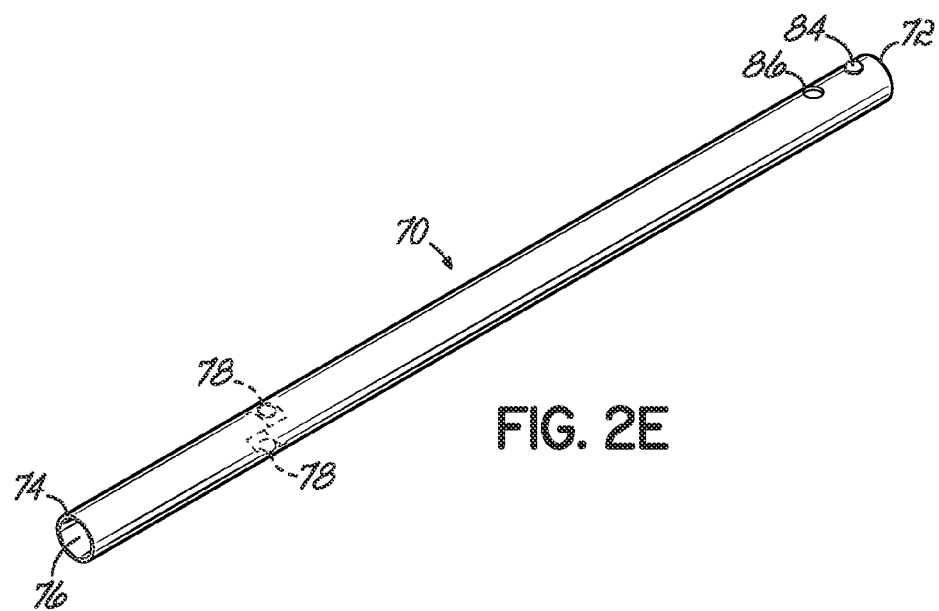
FIG. 2E illustrates one embodiment of a conduit.

Referring to FIG. 2A, a shunt 46 to drain aqueous fluid from the eye 10 has a proximal end 48, a distal end 50, and defines therein a passageway or lumen 52. Once implanted into the eye 10, the shunt 46 provides fluid communication between the anterior chamber 38 and the exterior of the eye 10. FIG. 2B illustrates a stylet 54 also having a proximal end 56 and a distal end 58. The stylet 54 is constructed and arranged to pass inside the shunt 46 and includes a sharp tip 60 at distal end 58 for penetrating the eye 10. FIG. 2C illustrates a meshed reservoir 62 having a curved top surface 64 and a flat bottom surface 66 defining an interior space 68 illustrated in FIG. 2D. The interior space 68 is adapted to contain fluid drained from the eye 10. FIG. 2E illustrates a collapsible conduit 70 with a proximal end 72, a distal end 74, and defines therein a lumen 76. The collapsible conduit 70 also includes detents 78 shown in phantom lines. The collapsible conduit 70 passes over the shunt 46 prior to implantation into the eye 10. The collapsible conduit 70 deforms under pressure assisting with deformation of shunt 46 during implantation of the shunt 46 into the eye 10.

Referring again to FIG. 2A, the shunt 46 is generally tubular having a lumen 52 defined throughout its length to facilitate the flow of liquid out of the eye 10. Commonly, the fluid flows out of the anterior chamber 38 of the eye 10. In other embodiments, the device may be used as a fluid conduit from other areas of the eye 10. In one embodiment, the shunt 46 is formed of a radially expandable mesh or mesh-like material that is able to control the flow rate of fluid out of the eye 10 by axially compressing until the lumen 52 is reduced or closed. The mesh or mesh-like material may be polymeric, metallic, or combinations of materials.

Examples of materials from which the mesh network may be prepared include, but are not limited to, one or a combination of a polymer based material, a metal, a shape memory alloy, silicone, or other biocompatible material that may be either biodegradable or non-biodegradable. Examples of non-biodegradable synthetic biocompatible polymers include, but are not limited to, silica, silicone, hydrogel, hilafilcon, hilafilcon B, synthetic polymers made from natural fats and oils, polyethylene, poly(alkylcyanoacrylates), polybutylcyanoacrylates, polyhexylcyanoacrylates, polyethylcyanoacrylate, polyisobutylcyanoacrylate, polycyanoacylate, silica, poly(D,L-lactide-coglycolide, silicone, polyvinylpyrrolidone, polyvinylalcohol, polycaprolactone, poly(glycolic acid) (PGA), poly(lactic acid) (PLA), copolymers of PGA and PLA, polydioxananone (PDS), poly(methylmethacrylate) (PMMA), poly(hydroxyethylmethacrylate) (HEMA), glyceroldimethacrylate (GDM), glycerol methacrylate (GMA), copolymerized PMMA with methacryloxypropyl tris(trimethysiloxy silane) (TRIS) PMMA-TRIS, MMA-TRIS doped with fluoromethacrylates, or polydimethylsiloxane (PDMS). Other naturally occurring polymers include, but are not limited to, collagen, mucopolysaccharides, condroitin sulfate, laminin, elastin, fibroin, keratins, hyaluranic acid, integrin, glucosaminoglycan, proteoglycans, fibronectin, hyaluronan, starches, cellulose, agar, alginate, carrageenan, pectin, konjac, gums, chitan, sulfated chitan, chitosan, polylactic acid, polyhydroxyalkanoates, silks, collegin/gelatin, reslin, palamino acids, wheat gluten, casein, soy, zein, serum albumin, cellulose, xanthum, dextran, gellan, levan, curd Ian, polygalactosamine, pullulan, elsinan, yeast glucans, acetoglycerides, waxes, emulsan, surfactants, lignin, tannin, humic acid, shellac, polygammaglutamic acid, or natural rubber. In addition, combining these materials, such as coating a metal mesh with a biocompatible polymer, may be used to provide materials for preparing shunt 46. In one embodiment, a portion or the entire shunt 46 may be coated in or on, or impregnated with, a medicament. For example, one or a combination of macrolides, antiproliferative agents, antiangiogenic agent, antibiotics, stimulatory factors, anti-inflammatory agent, etc. may be used.

Macrolides include, but are not limited to, Cyclosporin A (cyclosporine, topical formulation Arrestase®, Allergan Inc; Sigma-Aldrich (St. Louis Mo.), sirolimus (rapamycin, RAPA, Rapamune®), ascomycin (pimecrolimus, Immunomycin, FR-900520), tacrolimus (FK 506), an ethyl analog of tacrolimus, everolimus (RAD-001, SCZ RAD, Certican (Novartis, Basel Switzerland), an analog of sirolimus, erythromycin and its derivatives such as azithromycin and clarithromycin, lincomycin, dirithromycin, josamycin, spiramycin, diacetyl-midecamycin, troleandomycin, tylosin, roxithromycin, new macrolide antibiotic scaffolds and derivatives in development, including but not limited to the ketolides ABT-773 and telithromycin as described by Schonfeld and Kirst (Eds.) in Macrolide Antibiotics, Birkhauser, Basel Switzerland (2002); macrolides derived from leucomycins, as described in U.S. Pat. Nos. 6,436,906; 6,440,942; and 6,462,026 assigned to Enanta Pharmaceuticals (Watertown Mass.); lincosamides; biolimus, ABT-578 (methylrapamycin), and derivatives of rapamycin such as temsirolimus (CCI-779, Wyeth) and AP23573 (Ariad).

By way of illustration only, Cyclosporin A is an immunosuppressant and acts in a particular subset of T lymphocytes, the helper T cells, by inhibiting production of the cytokine interleukin 2. Each of Cyclosporin A and tacrolimus, another immunosuppressant, produce significant renal and hepatic toxicity when each is administered systemically; because of this toxicity, they are not administered together. Cyclosporin A has good penetration into the cornea but not into the anterior chamber, and does not increase intraocular pressure or cause cataracts. Its known toxicity had previously limited its use for other ocular diseases. The use of Cyclosporin A as a specific medicament for treatment of ocular disease with reduced toxicity has been described in co-pending U.S. patent application Ser. No. 10/289,772, which is expressly incorporated by reference herein in its entirety.

Examples of antiproliferative agents known to one skilled in the art include, but are not limited to, methotrexate, cyclophosphamide, ifosphamide, 5-fluorouracil, 5-fluorouridine, cytarabine, bleomycin, mitomycin-c, etc.

Examples of anti-inflammatory agents known to one skilled in the art include, but are not limited to, colchicine; a steroid such as triamcinolone (Aristocort®; Kenalog®), anecortave acetate (Alcon), betamethasone (Celestone®), budesonide cortisone, dexamethasone (Decadron-LA®;

Decadron® phosphate; Maxidex® and Tobradex® (Alcon)), hydrocortisone methylprednisolone (Depo-Medrol®, Sol-uMedrol®), prednisolone (prednisolone acetate, e.g., Pred Forte® (Allergan), Econopred and Econopred Plus® (Alcon), AK-Tate® (Akorn), Pred Mild® (Allergan), prednisone sodium phosphate (Inflamase Mild and Inflamase Forte® (Ciba), Metreton® (Schering), AK-Pred® (Akorn)), fluorometholone (fluorometholone acetate (Flarex® (Alcon), Eflone®), fluorometholone alcohol (FML® and FML-Mild®, (Allergan), Fluor OP®), rimexolone (Vexol® (Alcon)), medrysone alcohol (HMS® (Allergan)), lotoprednol etabonate (Lotemax® and Alrex® (Bausch & Lomb), and 11-desoxcortisol; an anti-prostaglandin such as indomethacin; ketorolac tromethamine; ((±)-5-benzoyl-2,3-dihydro-1H-pyrrolizine-1-carboxylic acid, a compound with 2-amino-2-(hydroxymethyl)-1,3-propanediol (1:1) (Acular® Allegan), Ocufen® (flurbiprofen sodium 0.03%), meclofenamate, fluorbiprofen, and the pyrrolo-pyrrole group of non-steroidal anti-inflammatory drugs; a non-steroidal anti-inflammatory drug such as derivatives of acetic acid (e.g. diclofenac and ketorolac (Toradol®, Voltaren®, Voltaren-XR®, Cataflam®)), salicylate (e.g., aspirin, Ecotrin®), proprionic acid (e.g., ibuprofen (Advil®, Motrin®, Medipren®, Nuprin®)), acetaminophen (Tylenol®), aniline (e.g., aminophenolacetaminophen, pyrazole (e.g., phenylbutazone), N-arylanthranilic acid (fenamates) (e.g., meclofenamate), indole (e.g., indomethacin (Indocin®, Indocin-SR®)), oxicam (e.g., piroxicam (Feldene®)), pyrrol-pyrrole group (e.g., Acular®), antiplatelet medications, choline magnesium salicylate (Trilisate®), cox-2 inhibitors (meloxicam (Mobic®)), diflunisal (Dolobid®), etodolac (Lodine®), fenoprofen (Nalfon®), flurbiprofen (Ansaid®), ketoprofen (Orudis®, Oruvail®), meclofenamate (Meclomen®), nabumetone (Relafen®), naproxen (Naprosyn®, Naprelan®, Anaprox®, Aleve®), oxaprozin (Daypro®), phenylbutazone (Butazolidine®), salsalate (Disalcid®, Salflex®), tolmetin (Tolectin®), valdecoxib (Bextra®), sulindac (Clinoril®), and flurbiprofin sodium (Ocufen®), an MMP inhibitor such as doxycycline, TIMP-1, TIMP-2, TIMP-3, TIMP-4; MMP1, MMP2, MMP3, Batimastat (BB-94), TAPI-2,10-phenanthroline, and marimastat.

Examples of anti-platelet derived growth factor (anti-PDGF) compounds include, but are not limited to, imatinib mesylate (Gleevec®), sunitinib malate (Sutent®) which has anti-PDGF activity in addition to anti-VEGF activity, and/or anti-leukotriene(s) such as genleuton, montelukast, cinalukast, zafirlukast, pranlukast, zileuton, BAYX1005, LY171883, and MK-571

Other agents that may be included are known to one skilled in the art and include, but are not limited to, transforming growth factor β (TGFβ), interleukin-10 (IL-10), aspirin, a vitamin, etc.

In one embodiment, a time-release drug delivery system is formulated with, in, on, etc. the mesh network to result in sustained release of the medicament(s) over a period of time. The formulation may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety, or lipids that may be formulated as microspheres or liposomes. As an illustrative example, sirolimus may be mixed with polyvinyl alcohol (PVA), the mixture then dried and coated with ethylene vinyl acetate, then cooled again with PVA. In a formulation for intraocular administration, the liposome capsule degrades due to cellular digestion providing a slow release drug delivery system, allowing the patient a constant exposure to the drug over time.

In one embodiment, one or more components of the device (e.g., the conduit, stylet, etc.) may be coated with an amniotic membrane as described in commonly owned U.S. patent application Ser. No. 10/874,724 hereby incorporated by reference herein in its entirety. In one embodiment, amniotic membrane is formulated as a tear drop spray by pulverizing and mixing with a physiological solution to form an emulsion. One or more surfactants may be added to reduce surface tension around the dispersed drops. The result is a condensed, non-adherent film that reduces coalescence and imparts electrical potential so mutual repulsion occurs.

The mesh may be in a variety of patterns. For example, apertures 80 of different sizes between interlocking fibers 82 of the mesh may be used. Alternatively, uniform aperture sizes may be used. The shunt 46 is not limited to a mesh pattern. An expandable spiral pattern can be used to construct the shunt 46 for alternative embodiments of the shunt 46. The apertures 80 shape can vary from parallelograms to oval shapes, circles, triangles, or any other geometric shape readily apparent to those skilled in this art. The mesh spiral design facilitates radial expansion and contraction of the shunt 46 in a manner analogous to operation of a Slinky™ toy. Such radial flexibility of the shunt 46 provides control of the flow of the fluid out of the eye 10 maintaining the shunt 46 so that it does not collapse and thus restrict the lumen.

Referring to FIG. 2B, the stylet 54 slides inside the lumen 52 of the shunt 46 during implantation of the shunt 46 in the eye 10. The stylet 54 has a tapered tip 60 allowing its use to penetrate through the sclera 12 into the anterior chamber 38 to implant shunt 46. In one embodiment, the stylet 54 is a 22-gauge solid needle. Those skilled in the art readily recognize that other gauge sizes of needles or other similar devices may be used in alternate embodiments (e.g., from about 1 μm to about 1 mm). In this embodiment, implanting shunt 46 into the anterior chamber 38 requires insertion of the stylet 54 through the portion of the sclera 12 behind the limbus 26. Removal of the stylet 54 occurs after the distal end 50 of the shunt 46 and the collapsible conduit 70, which surrounds the shunt 46, are placed at the desired depth inside the anterior chamber 38. The stylet 54 may be formed from different materials in different embodiments. For example, metals, polymers, glass, ceramics or any sufficiently rigid and biocompatible material providing adequate penetration of the eye tissue may be suitable for forming stylet 54.

FIG. 2C illustrates the reservoir 62 for coupling to the shunt 46 and the collapsible conduit 70 and holding the fluid drained from the eye 10. In this embodiment, the reservoir 62 has a domed shape, but other embodiments can use other shapes known to those skilled in the art. In this embodiment, the reservoir 62 has a locking mechanism 84, such as a snap lock, but other locking mechanisms can be used as known to those skilled in the art. The locking mechanism 84 connects to the proximal end 48 of the shunt 46 extending out of the eye 10 when the shunt 46 is implanted in the eye 10.

In the illustrated embodiment, the reservoir 62 is formed of a mesh material. In one embodiment, the mesh material allows the fluid from the eye 10 to slowly disperse out of the reservoir 62 into the surrounding tissue. In another embodiment, the mesh material collapses under pressure and expands when released from pressure, facilitating natural or mechanical expulsion of the fluid in the interior space 68. Pressing on the curved top surface 64 causes the curved top surface 64 to deflect forcing fluid out of the reservoir 62 when the shunt 46 has been disconnected. Alternatively, in other embodiments, the reservoir may be removed from the eye 10 for drainage, cleaning, replacement, etc. The mesh material may be similar or identical to the mesh material used in the shunt 46, but also can differ in other embodiments. The mesh material can be formed of a polymer, metal, silicone, shape memory alloy or other biocompatible material readily apparent to those skilled in this art. In addition, the reservoir 62 may be coated with macrolides, antiproliferative agents, amniotic membrane, other medicament agents, or a combination thereof.

Referring to FIG. 2E, the conduit 70 is generally tubular and defines a lumen 76 sized to allow the shunt 46 to pass inside. In one embodiment, the collapsible conduit is optional, and use only the shunt 46 is used. The conduit 70 is constructed and arranged so at least a portion of it is capable of collapsing around the shunt 46 to reduce or prevent flow through the shunt 46, thus reducing or preventing fluid flow out of the eye 10 when implanted inside the eye 10.

In one embodiment, the conduit 70 includes detents 78 for applying pressure to the outer surface 85 of the shunt 46 when the collapsible conduit 70 collapses under pressure. In one embodiment, the conduit 70 is constructed and arranged to collapse temporarily under external pressure and then regain its original form after removing the pressure. In another embodiment, the conduit 70 is constructed and arranged to bias inwardly, bringing the detents 78 into contact. The fluid pressure in the shunt 46 must obtain a certain threshold to overcome the internal bias of the collapsible conduit 70 to force the detents 78 apart and enable a fluid flow out of the eye 10. The conduit 70 may achieve these properties by being formed of a semi-solid material. The conduit 70 slides over the shunt 46 and attaches to the shunt 46 using a second locking mechanism 86, such as the illustrated snap lock system. The conduit 70 may also be screwed onto its counterpart.

In one embodiment, conduit 70 is formed of a resilient material, e.g., silicone or a polymer. Upon compression, either externally or through internal bias, the detents 78 move together. This reduces or closes the lumen 52 of shunt 46, thereby reducing or preventing fluid from flowing through the shunt 46. The conduit 70 resumes its original shape once the external compressive force is lessened or the internal fluid pressure subsides. In one embodiment, a medical professional restricts fluid flowing through the shunt 46 by applying pressure to the conduit 70 at one or more sites to cinch the shunt 46 closed. In another embodiment, the conduit 70 is self-regulating and opens and closes in response to changes in fluid pressure inside of the eye 10. In this embodiments, it operates is a manner analogous to a venous valve.

Figures 3A, 3B:
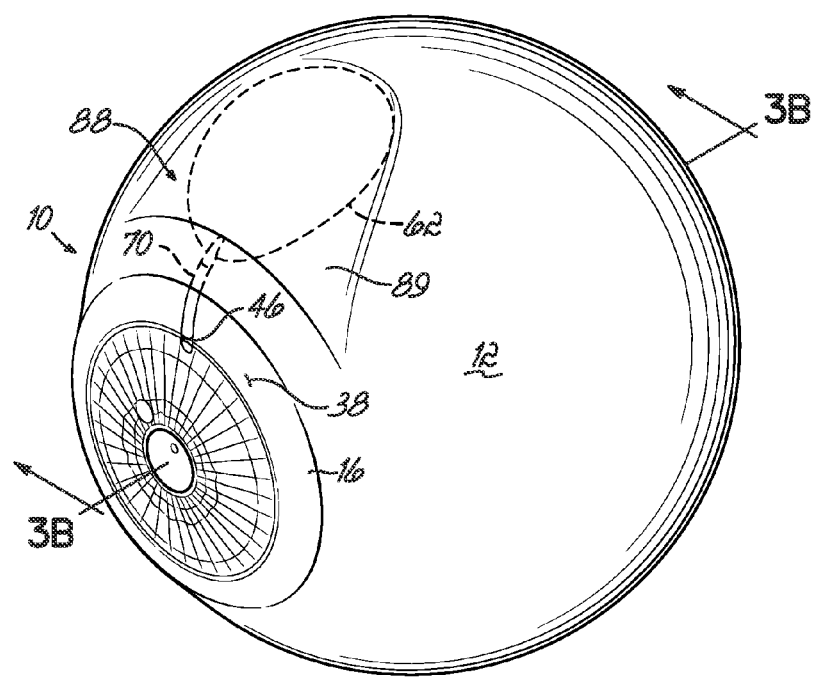
FIG. 3A illustrates an assembled fluid drainage device in a human eye.
FIG. 3B illustrates a cross section view of FIG. 3A.

Referring to FIGS. 3A and 3B, the assembled fluid drainage device 88 is positioned upon a human eye 10. The shunt 46 and conduit 70 have their distal ends 50, 74 placed into the anterior chamber 34 of the eye 10 through the sclera 12 behind the limbus 26 and their proximal ends 48, 72 extending out of the eye 10. The reservoir 62 is connected to the proximal end 72 of the conduit 70 via locking mechanism 84. The reservoir 62 lies under a lamella 89 formed in the sclera 12 of the eye 10 created by cutting through the conjunctiva 16. The conjunctiva 16 is closed after placing the reservoir 62 under the lamella 89 formed in the sclera 12 of the eye 10. Alternatively, shunt 26 may be inserted through the limbus under the conjunctiva without performing a lamellar dissection of the sclera. The fluid drainage device 88 facilitates draining of excess fluid accumulated inside of the eye 10 out of the shunt 46 and into the reservoir 62. The amount of fluid in the reservoir 62 can either be expelled manually or slowly dispersed through the interstices of the mesh.

FIG. 3B illustrates the distal end 50 of the shunt 46 in the anterior chamber 38 of the eye 10 and the proximal end of the shunt 46. In the illustrated embodiment, the shunt 46 inserts through the portion of the sclera 12 located above the pars plana 26 positioning the reservoir 62 away from the anterior chamber 38 underneath the sclera 12 and the conjunctiva 16. The distal end 50 of the shunt 46 lies inside of the anterior chamber 38. The fluid pressure is greater inside of the eye 10 than inside of the shunt 46 or the reservoir 62 creating fluid communication between the anterior chamber 34 and the reservoir 62. The fluid flows through the shunt 46 for collection inside of the reservoir 62. Positioning of reservoir 62 enables a medical professional to readily engage the reservoir 62 and disconnect the reservoir 62 from the shunt 46 and conduit 70. In one embodiment, external pressure is maintained on the conduit 70, keeping the shunt 46 closed. In another embodiment, an internal bias keeps the shunt 46 closed until the fluid pressure inside the eye 10 is sufficient to force the shunt 46 open. Reservoir emptying can occur by compressing the reservoir 62, removing and draining the reservoir 62, or through the fluid dispersing out through the mesh of the reservoir 62. If the reservoir 62 is removed, the reservoir 62 reconnects to the collapsible conduit 70 having an interior space 68 ready to receive additional fluid. Accordingly, regulating fluid flow is simplified and improved, reducing the likelihood of a "soft" eye or scarring due to the presence of inflammatory cytokines in the fluid retained in the eye.

Figure 4A:
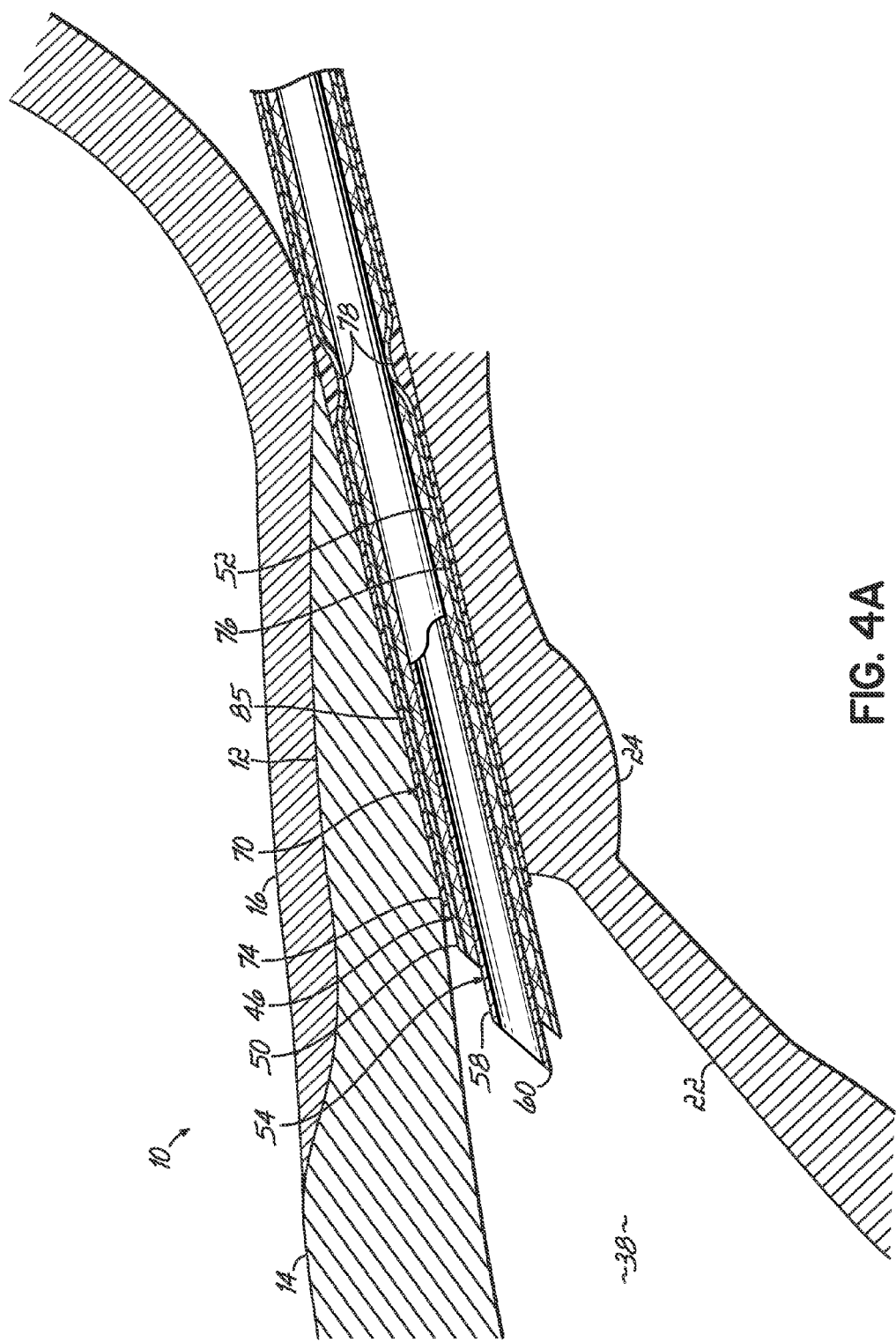
FIG. 4A illustrates implanting the shunt of FIG. 2A into a human eye using the stylet of FIG. 2B.
Figure 4C:
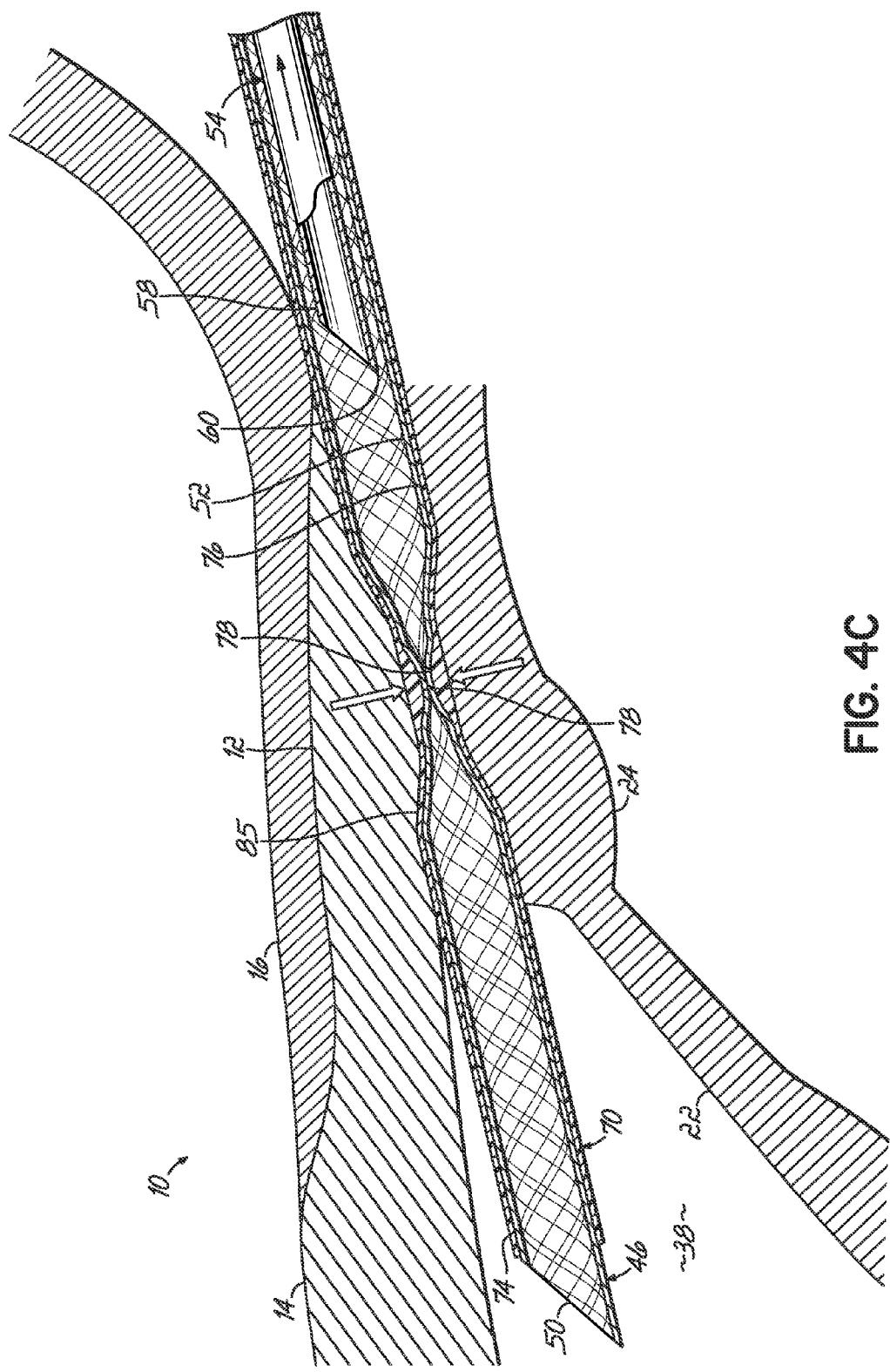
FIG. 4C illustrates collapsing a portion of the conduit of FIG. 2E.
Figure 4D:
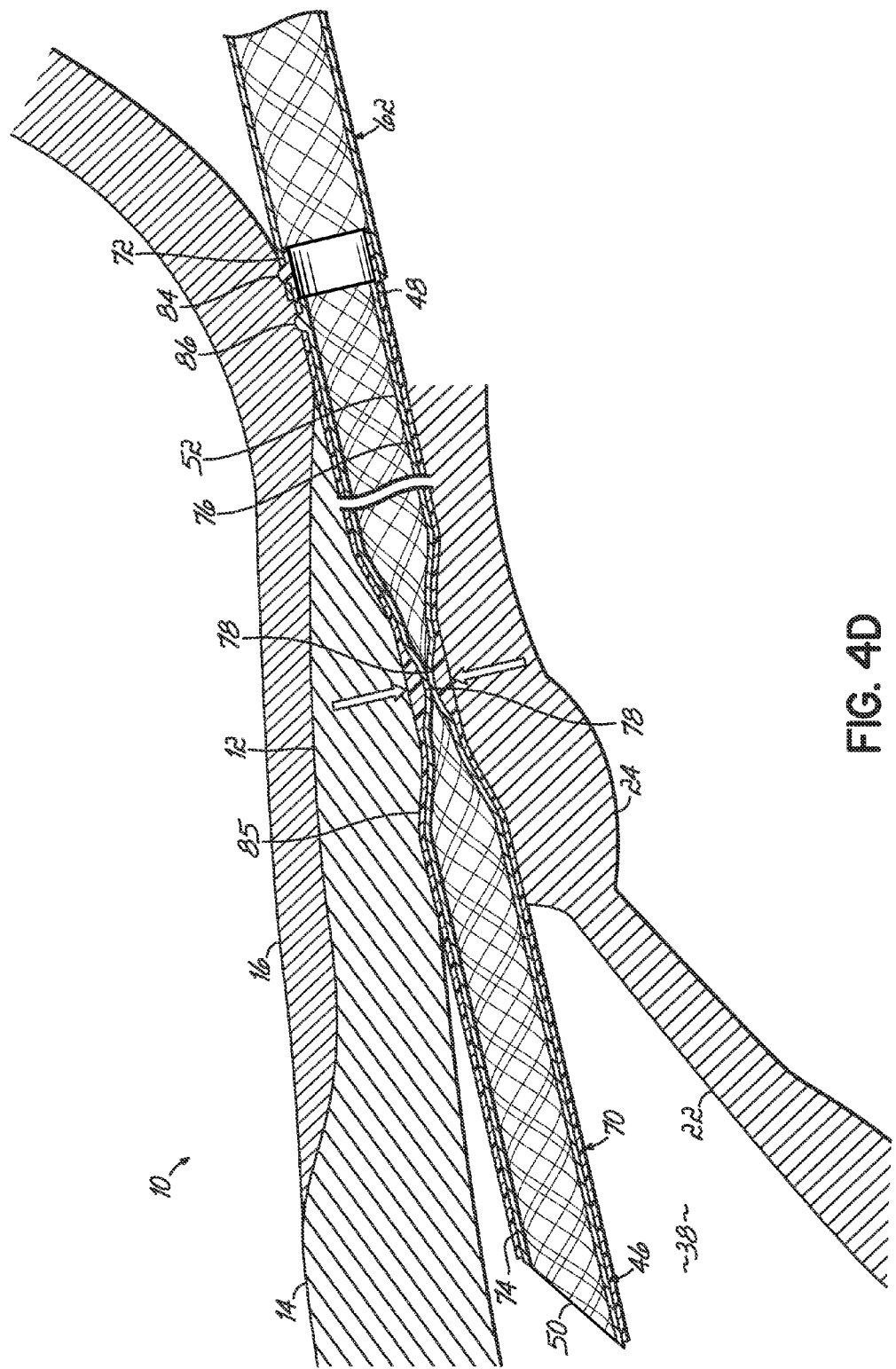
FIG. 4D illustrates attaching the reservoir of FIG. 2C to the shunt of FIG. 2A while the portion of conduit of FIG. 2E is collapsed.
Figure 4E:
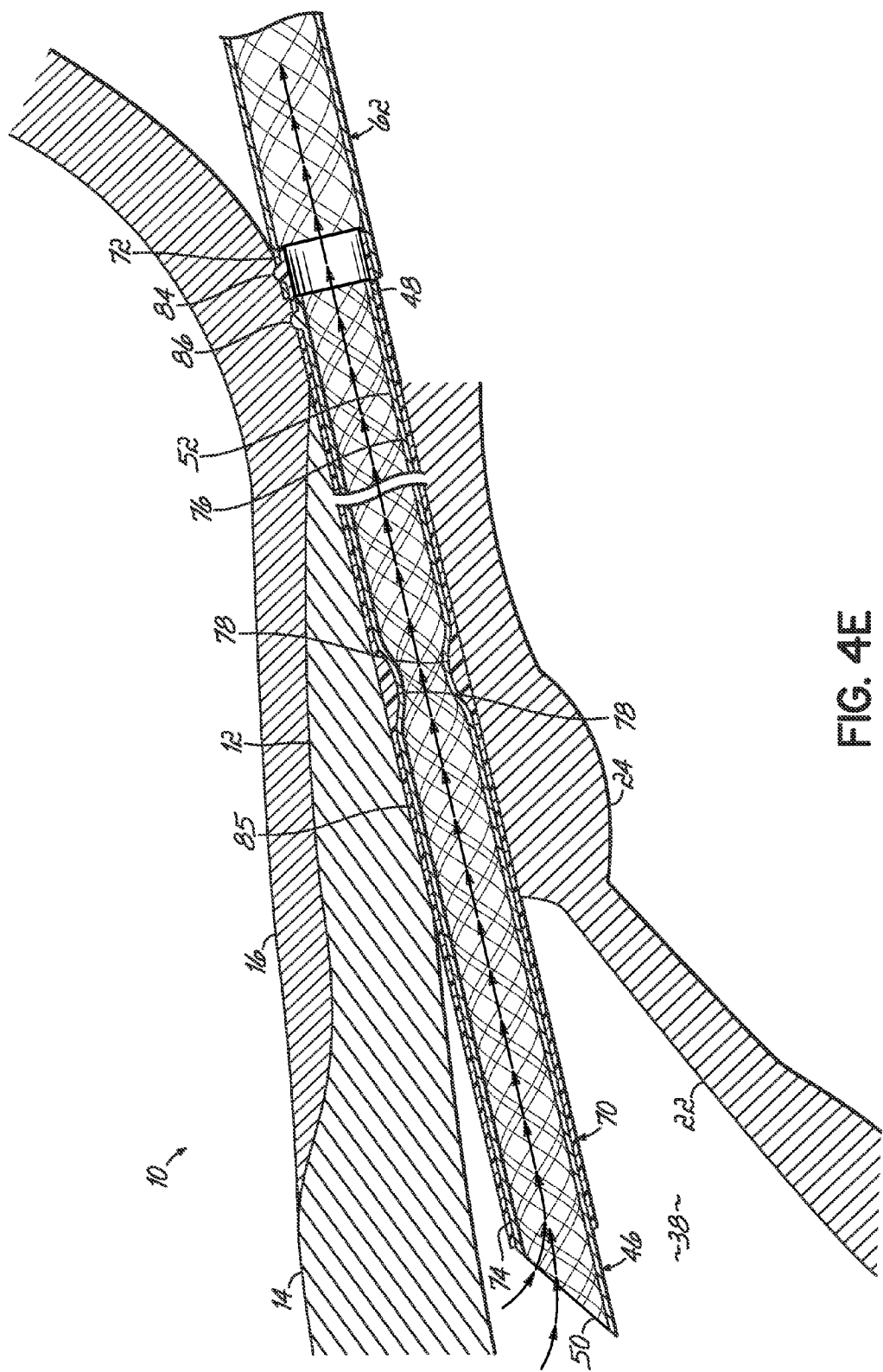
FIG. 4E illustrates allowing the portion of the conduit of FIG. 2F to open.

FIGS. 4A-4E describe one method of placing the fluid drainage device 88 onto the eye 10. Initially, the shunt 46 and conduit 70 are combined. The conduit 70 slides over the shunt 46 and snap locks onto the shunt 46 via the second locking mechanism 86. The stylet 54 is then inserted into the lumen 52 of the shunt 46. The conjunctiva 16 of the eye 10 is ballooned away from the sclera 12 using saline or a viscoelastic material. A small incision is then made in the conjunctiva 16 and the sclera 12 exposed. A lamella having one edge along the anterior chamber 38 is formed in the sclera 12 to contain the reservoir 60. FIG. 4A illustrates the sharp tip 60 of the stylet 54 penetrating the sclera 12 for introducing the distal end 50 of the shunt 46 into the anterior chamber 38 of the eye 10. FIG. 4B illustrates removal of the stylet 54 from the shunt 46 after implantation of the shunt 46 and conduit 70 into the anterior chamber 38. Removing the stylet 54 initiates fluid flow out of anterior chamber 38 and into shunt 46. As shown in FIG. 4C, pressure, either externally or from internal bias, on conduit 70 cinches the shunt 46 closed and reduces or prevents fluid flowing out of the proximal end 48 of the shunt 46. The detents 78 of the conduit 70 apply pressure to the shunt 46 and cinch the shunt 46 closed. The locking mechanism 84 of the reservoir 62 attaches to the collapsible conduit 70 while the shunt 46 is still cinched closed as illustrated in FIG. 4D. FIG. 4E illustrates the collapsible conduit 70 resuming its original shape after releasing pressure from the collapsible conduit 70. The shunt 46 opens and fluid from the eye 10 flows through the shunt 46 and into the interior space 68 of the reservoir 62.

In one embodiment, shunt 46, conduit 70, and/or reservoir 62 contain one or more medicaments, examples of which were previously described. The medicaments may be formulated with the mesh material, located in or on the mesh, contained within reticulations (e.g., by a tether), etc. The medicaments may microcapsules, microparticles, nanocapsules, nanoparticles, liposomes, etc., any of which may be coated or uncoated. For example, a drug may be formulated as nanoparticles or nanocrystals of pharmaceutically active compounds, and/or nanoscale dispersions, encapsulations, and emulsions (e.g., to limit or prevent aggregation or reaggregation of crystals, to incorporate a stabilizer, etc). The drug(s) may be combined with albumin or another non-toxic solvent to form nanoparticles in a solvent-free formulation of a toxic drug. The drugs may be formulated as sugar-derived nano compounds that may shield proteins and small molecules from rapid breakdown. The drugs may be rendered more soluble in a nanocrystal formulation by decreasing drug particle size and hence increasing the surface area thereby leading to increased dissolution. These techniques are known to one skilled in the art as disclosed in, for example, U.S. Pat. Nos. 6,822,086; 6,753,006; 6,749,868; 6,592,903; 6,537,579; 6,528,067; 6,506,405; 6,375,986; 6,096,331; 5,916,596; 5,863,990; 5,811,510; 5,665,382; 5,560,933; 5,498,421; 5,439,686; and 5,362,478; and U.S. patent application Ser. Nos. 10/106,117; 60/147,919; and 08/421,766, each of which is expressly incorporated by reference herein in its entirety.

Other variations or embodiments of the invention will also be apparent to one of ordinary skill in the art from the above figures, description, and example. Thus, the forgoing embodiments are not to be construed as limiting the scope of this invention.

What is claimed is:

1. A ocular device comprising
   a shunt defining a lumen providing fluid communication between an interior chamber of an eye and an exterior of the eye;
   a stylet received within the lumen of the shunt for implanting the shunt in the eye;
   a conduit including a lumen through which the shunt and stylet are disposed while implanting the shunt and the conduit in the eye, the conduit having a collapsible portion for collapsing around the shunt at a collapsing location proximal a distal end of the shunt to reduce or prevent flow through the shunt, the conduit extending along the length of the shunt from a position proximal the collapsing location to a position distal the collapsing location; and
   a reservoir operatively coupled to the conduit;
   wherein removing the stylet after implanting initiates fluid drainage from the interior chamber of the eye through the shunt into the reservoir.

2. The device of claim 1 wherein the shunt is radially expandable.

3. The device of claim 1 wherein the reservoir contains at least one medicament.

4. The device of claim 1 wherein at least one of the reservoir, shunt, or conduit contains at least one medicament.

5. The device of claim 1 wherein at least one of the reservoir, shunt, or conduit is at least partially coated with amniotic membrane.

6. The device of claim 1 wherein the interior chamber of the eye is the anterior chamber.

7. The device of claim 1 wherein the reservoir is meshed.

8. The device of claim 1 wherein the conduit includes a detent at the collapsible portion of the conduit that applies pressure to an outer surface of the shunt, the detent extending outwardly into the lumen from an inner surface of the conduit.

9. The device of claim 8 wherein the conduit is configured to collapse under external pressure applied at the collapsible portion so that the detent applies increased pressure to the outer surface of the shunt.

10. The device of claim 9 wherein the conduit collapses resiliently under the external pressure such that the collapsible portion regains its original form after the external pressure is removed thereby decreasing the pressure applied to the outer surface of the shunt.

11. The device of claim 8 wherein the conduit is biased radially inwardly at the collapsible portion to apply increased pressure against the outer surface of the shunt wherein the inward bias of the conduit is overcome when fluid pressure in the shunt obtains a predetermined threshold thereby enabling increased flow out of the eye.

12. An ocular device comprising
    a radially expandable shunt defining a lumen providing fluid communication between an interior chamber of an eye and an exterior of the eye;
    a conduit having an elongated, tubular shape with at least a portion of the conduit being collapsible, the conduit including a lumen through which the shunt passes; and
    a reservoir operatively coupled at a proximal location to the conduit;
    wherein fluid from the interior chamber of the eye flows through the shunt into the reservoir.

13. The device of claim 12 further comprising a stylet received into the lumen of the shunt and the conduit for implanting the device in the eye.

14. The device of claim 12 wherein at least one of the shunt or reservoir is meshed.

15. The device of claim 12 wherein at least one of the shunt, conduit, or reservoir contains at least one medicament.

16. A method for fluid drainage from an eye, the method comprising
    positioning a device in an eye, the device comprising
       a shunt defining a lumen,
       a conduit including a lumen through which the shunt passes, at least a portion of the conduit being partially collapsible and operatively coupled to the shunt for collapsing around the shunt at a location between proximal and distal ends of the conduit to reduce or prevent flow through the shunt,
       a stylet received within the lumen of the shunt and the conduit, the stylet penetrating the eye to position the device;
    pressurizing the conduit;
    removing the stylet from the device; and
    connecting a reservoir to the collapsible conduit for receiving fluid from the eye.

17. The method of claim 16 wherein the device is positioned under a conjunctiva, under a scleral lamella, or under both a conjunctiva and scleral lamella, in an interior chamber.

18. The method of claim 16 wherein at least one of the shunt, conduit, or reservoir contains at least one medicament, the medicament eluted by fluid flow.

19. The method of claim 16 further comprising incising a conjunctiva to expose a sclera, and incising the sclera to form a lamella extending from the anterior chamber to the retina.

20. The method of claim 16 further comprising positioning the device under the conjunctiva; and closing the incision formed in the conjunctiva.

* * * * *